United States Patent [19]

Wang et al.

[11] Patent Number: 5,804,451
[45] Date of Patent: Sep. 8, 1998

[54] OPTICAL MEASURING METHOD FOR MEVALONIC ACID

[75] Inventors: Yung Xiang Wang; Xiaoming Dou; Masayuki Yagi, all of Kyoto, Japan

[73] Assignee: Kyoto Dai-Ichi Kagaku Co., Ltd., Kyoto, Japan

[21] Appl. No.: 832,189

[22] Filed: Apr. 8, 1997

[30] Foreign Application Priority Data

Apr. 10, 1996 [JP] Japan ................................ 8-114106

[51] Int. Cl.⁶ .................................................. G01N 21/65
[52] U.S. Cl. ............................ 436/93; 436/129; 436/164; 436/174
[58] Field of Search ............................. 436/93, 129, 164, 436/174, 176, 909; 356/301

[56] References Cited

U.S. PATENT DOCUMENTS

| 4,847,198 | 7/1989 | Nelson et al. | 356/301 |
| 5,149,641 | 9/1992 | Endo et al. | 435/125 |

FOREIGN PATENT DOCUMENTS 0 637 742  2/1995  European Pat. Off. .

OTHER PUBLICATIONS

Spencer, Thomas "Feasibility of an immunoassay for mevalonolactone" Chemical Abstracts, vol. 127, abstract No. 146700r, Sep. 15, 1997.

Patent Abstracts of Japan, vol. 095, No. 009, Oct. 31, 1995 & JP 07–159400 A (S R L:KK), Jun. 23, 1995.

*Primary Examiner*—Jeffrey Snay
*Attorney, Agent, or Firm*—Nikaido, Marmelstein, Murray & Oram LLP

[57] ABSTRACT

Acid is added to a target sample such as urine, blood plasma or serum for converting mevalonic acid contained in the sample to lactone mevalonate, and the sample is irradiated with near infrared Raman excitation light, for determining mevalonic acid by measuring generated Raman scattered light. This method employs no mediatory reaction with simple pretreatment, requires no high-priced measuring apparatus, and can determine mevalonic acid in a short time.

12 Claims, 12 Drawing Sheets

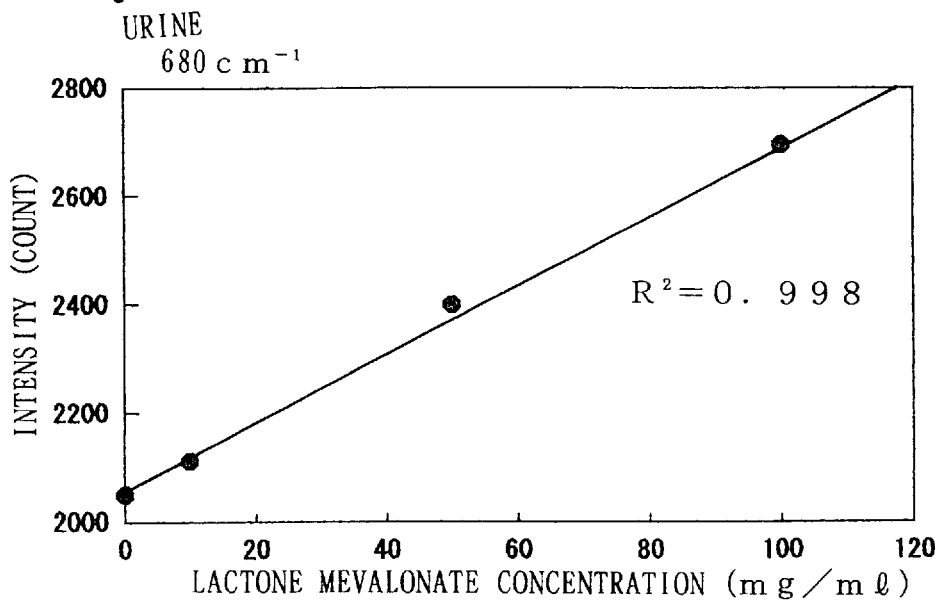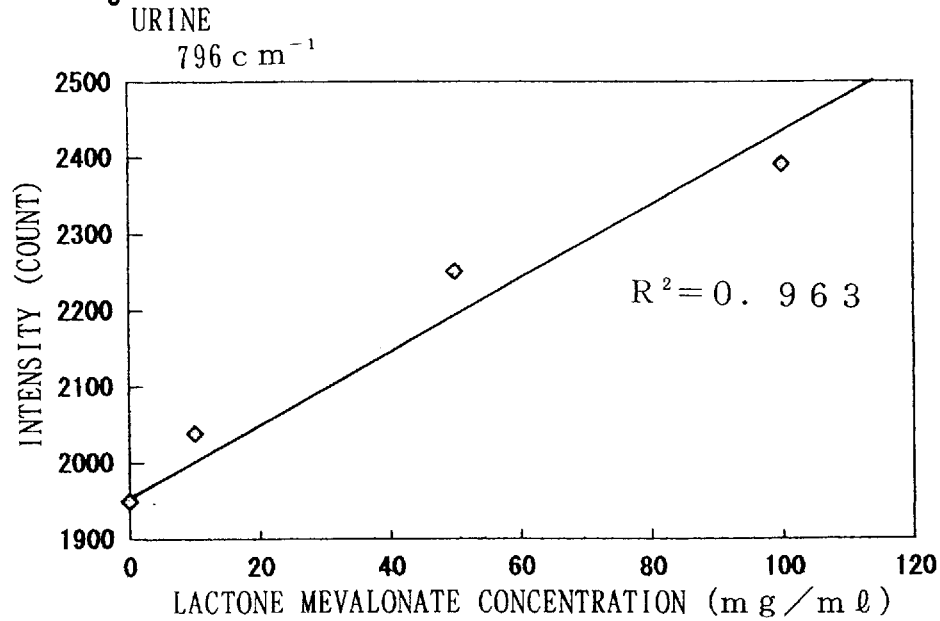

OPTICAL MEASURING METHOD FOR MEVALONIC ACID

BACKGROUND OF THE INVENTION

1. Field of the Invention

The present invention relates to a method of optically quantitatively measuring mevalonic acid which is contained in a sample such as a body fluid through Raman scattered light in the field of clinical tests. The body fluid sample may be prepared from urine, blood plasma or serum.

2. Description of the Background Art

Mevalonic acid, which is an intermediate product in a cholesterol biosynthetic pathway, is synthesized when a thioester group of 3-hydroxy-3-methylglutaryl coenzyme A is reduced with 3-hydroxy-3-methylglutaryl coenzyme A reductase which is a regulatory enzyme of sterol biosynthesis. Intravital cholesterol is biosynthesized through the aforementioned pathway, or ingested through food.

It is important to determine mevalonic acid which is contained in blood or urine, in evaluation of a cholesterol biosynthetic quantity.

Mevalonic acid may be determined by a measuring method through antigen-antibody reaction (refer to Japanese Patent Laying-Open Gazette Nos. 6-273417 (1994), 5-199869 (1993) etc.). However, this method is inferior in measuring accuracy due to interposition of the antigen-antibody reaction, which is mediatory reaction, and participation of an antibody with respect to an enzyme related to a fat metabolic system or the like. Further, this method requires an operation such as B-F separation, i.e., separating an immune complex resulting from the antigen-antibody reaction with mevalonic acid from the antibody not reacted with mevalonic acid.

A method of converting mevalonic acid to a derivative and thereafter separating and determining the same by a GC-MS (gas chromatograpy-mass spectrometry) method or through liquid chromatography is also known as a measuring method employing no mediatory reaction. In such a measuring method, however, mevalonic acid must be trimethylsilylated through complicated pretreatment or lactonized and thereafter dehydrated (refer to Japanese Patent Laying-Open Gazette No. 7-159400 (1995)). Further, separation is required in advance of such measurement, and hence the target substance contained in a mixed sample cannot be directly determined.

Mevalonic acid is lactonized and thereafter dehydrated through pretreatment to be brought into a structure having UV absorption, so that the same can be detected by a UV detector after separated through liquid chromatography. However, liquid chromatography-UV detection is insufficient in specificity also in the method of measuring mevalonic acid through no mediatory reaction.

On the other hand, Raman scattered light is specific to a substance.

SUMMARY OF THE INVENTION

An object of the present invention is to provide a method of determining mevalonic acid, which can quantitatively measure mevalonic acid in a short time with high specificity and through simple pretreatment while requiring no separation such as liquid chromatography in advance of detection as a direct method employing no mediatory reaction.

According to the present invention, mevalonic acid which is contained in a target sample is converted to a derivative, i.e., lactone mevalonate, and the sample is thereafter irradiated with Raman excitation light, for determining mevalonic acid by measuring generated Raman scattered light.

Mevalonic acid is so instable that its structure is readily changed due to influence by a contaminant or a coexistent contained in the sample, or pH. According to the present invention, mevalonic acid is converted to lactone mevalonate so that its Raman scattering is measured, for stabilizing mevalonic acid contained in the sample by converting the same to a lactone type.

In order to derive lactone mevalonate from mevalonic acid, the sample is acid-treated. The acid treatment can be carried out by adding acid such as hydrochloric acid, hydrogen chloride gas, sulfuric acid or perchloric acid, or a phosphoric acid buffer solution of pH 2 to 3 to the sample or bringing the sample into contact with solid acid such as ion exchange resin. The most preferable acid treatment is a method employing hydrochloric acid or hydrogen chloride gas which scatters no Raman light. In particular, hydrogen chloride gas has an advantage of diluting no sample.

A preferable sample is prepared from blood plasma, serum or urine.

When the sample is prepared from a body fluid such as blood or urine, the Raman excitation light which is applied to the sample is preferably prepared from near infrared light, in order to suppress generation of fluorescence from the sample thereby detecting Raman scattered light in high sensitivity.

Quantitative measurement is performed by a method of previously selecting a wavenumber having excellent correlation between the concentration and the Raman spectral intensity as to lactone mevalonate, irradiating the sample with Raman excitation light, and determining the mevalonic acid concentration in the sample through a calibration curve previously formed as to the Raman spectral intensity and the lactone mevalonate concentration at the selected wavenumber.

The shift wavenumber of the Raman scattered light measured for determining lactone mevalonate is preferably selected from the range of 650 to 700 $cm^{-1}$, 730 to 790 $cm^{-1}$, 1000 to 1100 $cm^{-1}$, 1100 to 1190 $cm^{-1}$, 1220 to 1300 $cm^{-1}$, 1320 to 1500 $cm^{-1}$, 1690 to 1750 $cm^{-1}$ or 2900 to 3000 $cm^{-1}$.

The pretreatment employed in the present invention, which is merely adapted to convert mevalonic acid to lactone mevalonate, can be performed through an extremely simple operation of acid-treating the sample. The reaction is as follows:

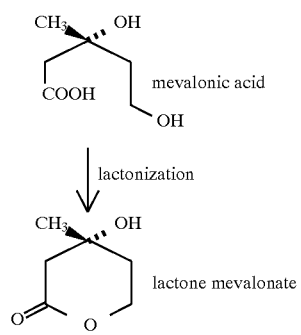

A signal specific to the substance of lactone mevalonate is directly measured through no mediatory reaction, whereby specificity is high, errors are hardly included, and influence by a contaminant or a pseudo substance having a similar bonding site with the antibody can be avoided.

Further, mevalonic acid can be measured in a short time since the sample is simply irradiated with the excitation light so that Raman scattered light is measured.

Among obtained Raman peaks, those appearing around 600 to 700 $cm^{-1}$, around 730 to 790 $cm^{-1}$, around 1070 $cm^{-1}$, around 1130 $cm^{-1}$, around 1160 $cm^{-1}$, around 1250 $cm^{-1}$, around 1350 $cm^{-1}$, around 1380 $cm^{-1}$, around 1400 $cm^{-1}$, around 1480 $cm^{-1}$, around 1720 $cm^{-1}$, around 2940 $cm^{-1}$ and around 2980 $cm^{-1}$ are conceivably derived from vibrations of C—C=O, a six-membered ring, $CH_3$, C—C—O, C—C(=O)—C, $CH_2$, OH, $CH_3$, CH, $CH_2$, C=O, $CH_2$ and $CH_3$ respectively.

According to the present invention, mevalonic acid contained in a target sample is converted to a derivative, i.e., lactone mevalonate, the sample is irradiated with Raman excitation light, and generated Raman scattered light is measured for determining mevalonic acid, whereby it comes to that lactone mevalonate is directly measured through no mediatory reaction, errors are hardly included, and influence by a contaminant or a pseudo substance having a similar bonding site with an antibody can be avoided.

Further, the sample is merely irradiated with excitation light so that Raman scattered light specific to the substance is measured, whereby specificity is high and mevalonic acid can be measured in a short time.

The pretreatment for converting mevalonic acid to lactone mevalonate is merely acid treatment of adding acid or the like, and its operation is simple. Lactone mevalonate is stable and a standard sample is easy to obtain, favorably for quantitative measurement.

The foregoing and other objects, features, aspects and advantages of the present invention will become more apparent from the following detailed description of the present invention when taken in conjunction with the accompanying drawings.

BRIEF DESCRIPTION OF THE DRAWINGS

FIGS. 12A and 12B show results employing peaks at shift wavenumbers of 680 $cm^{-1}$ and 769 $cm^{-1}$ respectively, for illustrating the correlation between peak intensities and lactone mevalonate concentrations of Raman spectra in standard samples prepared by dissolving lactone mevalonate in urine.

DESCRIPTION OF THE PREFERRED EMBODIMENTS

FIGS. 1 to 6 show some exemplary measuring apparatuses for carrying out the measuring method according to the present invention.

Figure 1:
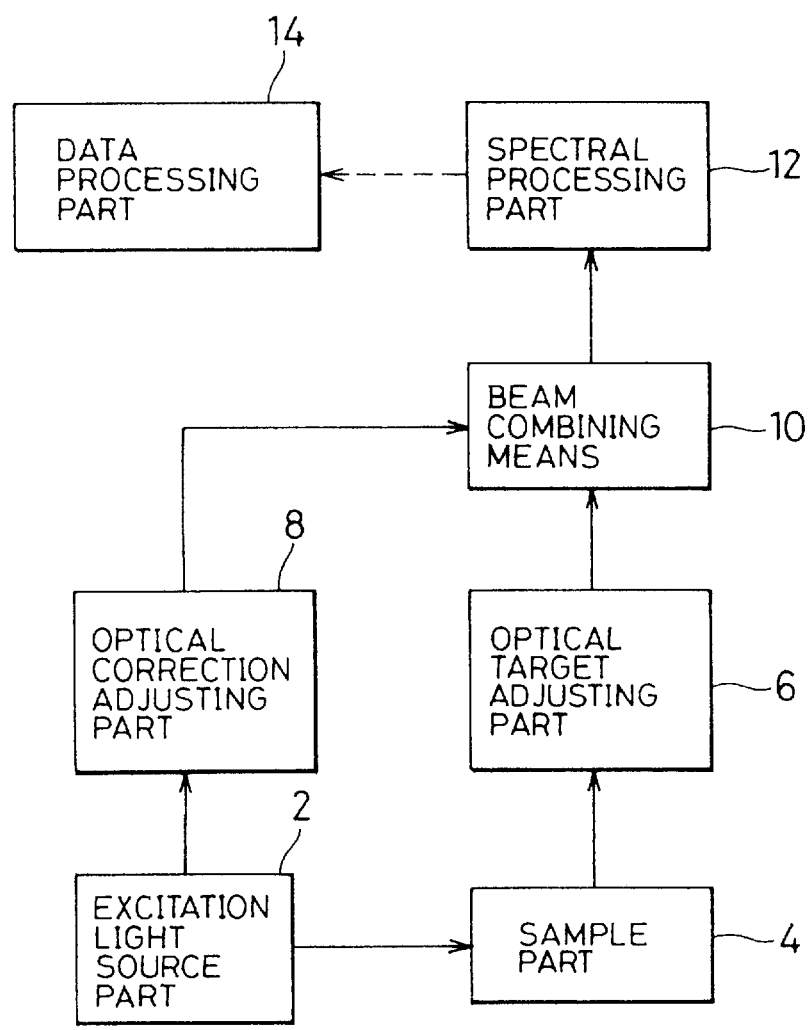
FIG. 1 is a block diagram schematically showing a measuring apparatus for carrying out the present invention.

FIG. 1 schematically shows a measuring apparatus comprising an excitation light source part 2 for emitting single-wavelength light having an excitation light source and a beam splitter for splitting a beam from the excitation light source into a sample beam and a correction beam, a sample part 4 for irradiating a sample with the sample beam, an optical target adjusting part 6 having filter means for removing the same wavelength component as the excitation light from scattered light generated from the sample irradiated with the sample beam and extracting target light containing fluorescence and Raman scattered light and an optical system for adjusting a beam, an optical correction adjusting part 8 for adjusting the correction beam split by a half mirror in the excitation light source part 2, beam combining means 10 for placing the beam outgoing from the optical target adjusting part 6 and the correction beam outgoing from the optical correction adjusting part 8 on the same optical axis, a single spectral processing part 12 having a spectroscope for separating the beam outgoing from the beam combining means 10 into its spectral components and a detector for detecting spectral light separated by the spectroscope, and a data processing part 14 having a function of correcting the intensity of the target light with reference to a detected intensity of an excitation light component in a spectrum detected by the detector of the spectral processing part 12.

The correction beam is adapted to correct fluctuation of the light emission intensity of the light source, and the beam splitter provided on the excitation light source part 2, the optical correction adjusting part 8 and the beam combining means 10 are unnecessary if such correction is not made.

The filter means provided on the optical target adjusting part 6 is preferably formed by any of a holographic notch filter including an excitation light wavelength in its notch region, a cut filter including the excitation light wavelength and blocking a shorter wavelength side, a bandpass filter having characteristics of transmitting and removing an excitation light wavelength component and reflecting a target light component, and a holographic beam splitter for removing the excitation light wavelength by transmission or reflection.

The spectral processing part 12 is preferably formed by a polychrometer comprising a multi-channel photodetector for simultaneously detecting target wavelength regions. When the spectral processing part 12 is formed by a polychrometer, the target wavelength regions can be simultaneously measured, and a target light spectrum of a prescribed region and the excitation light can be simultaneously detected. Consequently, no difference is caused between detection times for respective wavelengths of the target light and that for the excitation light. If difference may be caused between the detection times for the respective wavelengths of the target light and that for the excitation light, however, a wavelength scanning type spectroscope and a single-channel photodetector may be provided as the spectral processing part 12 for successively detecting the target wavelength regions.

The holographic notch filter is adapted to block only a desired wavelength region while transmitting wavelength light in other regions. When a holographic notch filter which is so set as to include the excitation light wavelength in the blocked region (notch region) is employed, the beam outgoing from the optical target adjusting part 6 includes no excitation light component but only the target light component. On the other hand, the correction beam, which includes only the excitation light from the light source not through the sample, is not dependent on the sample but expresses intensity fluctuation of the light source in fidelity.

FIGS. 2 to 6 show concrete examples illustrating the block diagram of FIG. 1 in detail.

Figure 2:
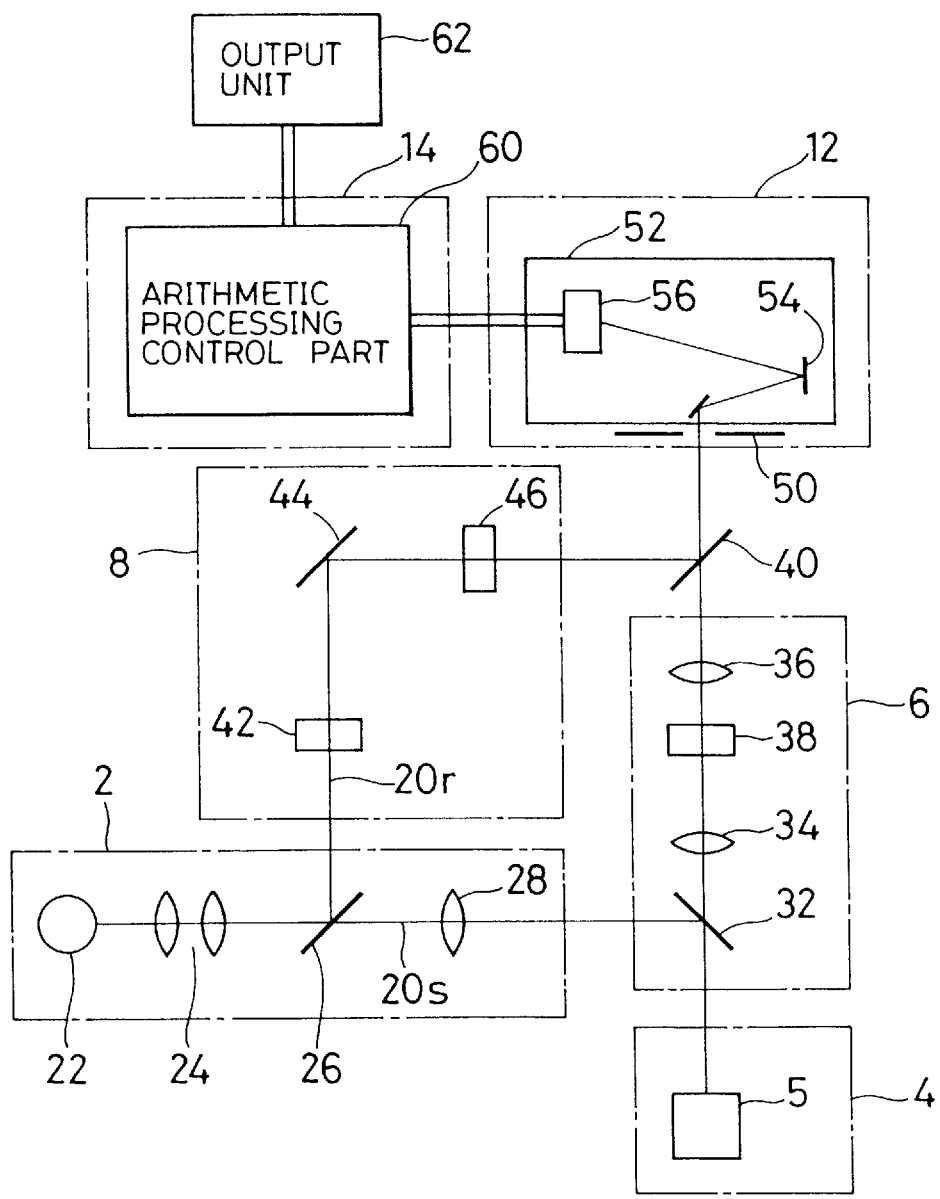
FIG. 2 is an arrangement diagram showing a measuring apparatus employing a holographic notch filter as filter means of an optical target adjusting part for receiving target light in a direction of 180 degrees to excitation light with respect to a sample.

FIG. 2 illustrates an embodiment employing a holographic notch filter including an excitation light wavelength in its notch region or a cut filter including the excitation light wavelength and blocking a shorter wavelength side as filter means of an optical target adjusting part 6 for receiving target light in a direction of 180 degrees to the excitation light with respect to a sample. An excitation light source part 2 is provided with a light source 22, and a half mirror 26 is arranged as a beam splitter for splitting the excitation light from the light source 22 into a sample beam 20s and a correction beam 20r.

The light source 22 is formed by a laser unit, for example. The laser unit can be prepared from an Ar ion laser unit, a Kr ion laser unit, an He—Ne laser unit, an He—Cd laser unit, an Nd:YAG laser unit, or a semiconductor laser unit which are continuously oscillating lasers, or a pulse laser, and can be selected from laser units of a wide wavelength range over near ultraviolet to near infrared regions. As a light source other than the laser unit, a light source such as a halogen lamp generating multi-wavelength light can be combined with a spectroscope.

The wavelength of the excitation light is preferably at least 800 nm, i.e., in a longer wavelength region exceeding the near infrared region. The reason for this is as follows: A vital component has high florescence and exhibits high fluoroemission efficiency when excited with visible light such that the spectrum is readily influenced by fluorescence, while the fluoroemission efficiency is reduced and the influence by fluorescence can be reduced when the vital component is excited with light of a longer wavelength region exceeding the near infrared region. Consequently, the background of Raman scattered light measurement is reduced and the signal-to-noise ratio of Raman scattered light detection is improved to be suitable for analysis of a microcomponent. Further, this excitation wavelength region has smaller photon energy as compared with the visible region, and hence damage of the sample is reduced. Consequently, sample damage is small as compared with visible light excitation Raman spectroscopy and influence by fluorescence is also small, to be suitable for measurement of a vital substance. Further, influence by external light such as fluorescent light which becomes stray light can also be reduced.

A near infrared semiconductor laser diode is a preferable example having an oscillation wavelength of at least 800 nm, and that having an oscillation wavelength of 800 to 1600 nm is preferable. GaAs/AlGaAs, InGaAs or InGaAsP can be employed as such a near infrared semiconductor laser diode. When a laser diode is employed, the cost can be reduced with a smaller space, and a compact Raman spectroscopic measuring apparatus can be implemented. While the laser diode may be instable in oscillation intensity, such instability of oscillation intensity can be corrected by detecting the light source intensity through a monitor and standardizing the Raman scattered light detection intensity with the light source intensity.

A light source condenser lens 24 and a convergent lens 28 are arranged on the excitation light source part 2 through the half mirror 26, in order to converge a sample beam 20s on a sample 5 provided in a sample part 4. The sample 5 is stored in a cell and set in the sample part 4.

The sample beam 20s from the excitation light source part 2 is reflected by a half mirror 32 which is arranged on an optical target adjusting part 6 and applied to the sample 5 provided in the sample part 4. The optical target adjusting part 6 is provided with condenser lenses 34 and 36, in order to converge scattered light from the sample 5 which is transmitted through the half mirror 32 on an inlet slit 50 of a spectroscope 52. A holographic notch filter 38 which is so set as to include the wavelength of the excitation light in its notch region is arranged in the optical target adjusting part 6 between the condenser lenses 34 and 36, as a filter for removing the same wavelength component as the excitation light and taking out target light. The holographic notch filter is available on Kaiser Optical Systems, Inc., U.S.A., for example. The holographic notch filter 38 has characteristics of completely blocking wavelength light included in the notch region and transmitting at least 80% of light of wavelength regions other than the notch region, for example.

A half mirror 40 is arranged between the condenser lens 36 of the optical target adjusting part 6 and the inlet slit 50 of the spectroscope 52 as beam combining means, so that the target light is transmitted through the half mirror 40 and incident upon the spectroscope 52.

A optical correction adjusting part 8 is adapted to guide the correction beam 20r which is split by the half mirror 26 in the excitation light source part 2 to the half mirror 40 of the beam combining means. This optical correction adjusting part 8 is provided with an extinction filter 42 for attenuating the light quantity, a bandpass filter 46 for blocking wavelength light generated in the half mirror 26 of the excitation light source part 2 and blocking a sideband from a laser beam when the light source 22 is formed by a laser unit, and a mirror 44 for bending an optical path. The correction beam 20r which is guided to the inlet slit 50 by the optical correction adjusting part 8 through the half mirror 40 is condensed on the inlet slit 50 by the light source condenser lens 24.

The target light outgoing from the optical target adjusting part 6 and the correction beam 20r guided from the optical correction adjusting part 8 are guided onto the same optical axis in the half mirror 40, and guided to the spectroscope 52 of a spectral processing part 12 through the inlet slit 50. The spectroscope 52, which is a polychrometer, comprises a diffraction grating 54 for separating incident light into its spectral components, and a multi-channel photodetector 56 provided with a plurality of photodetection elements along a dispersion direction of the diffraction grating 54, in order to simultaneously detect the spectral components separated by the diffraction grating 54 over a prescribed wavelength region. While the diffraction grating 54 shown in FIG. 2 is a concave diffraction grating, a spectroscope called a Czerny-Turner type combining a flat diffraction grating with a spherical mirror or a spectroscope employing a transmission diffraction grating is also employable.

In order to detect Raman scattered light by excitation light of the near infrared region, photodetection elements of Ge, InGaAs or PbS, a single-channel detector such as a photomultiplier having wavelength sensitivity in 300 to 1700 nm, or a multi-channel detector such as a photodetector array of Ge, InGaAs or PbS can be employed.

Numeral 60 denotes an arithmetic processing control part for controlling operations of the respective parts and processing a signal detected by the photodetector 56. This arithmetic processing control part 60 also includes a function for serving as a data processing part for correcting a detected intensity of the target light with reference to that of the excitation light component in the spectrum detected by the photodetector 56, for operating a Raman scattering spectrum with corrected fluctuation of the light source, and qualitatively or quantitatively analyzing the sample 5 with reference to the target light intensity. Numeral 62 denotes an output unit such as a printer or a display for outputting the data processed in the arithmetic processing control part 60.

In the embodiment shown in FIG. 2, the holographic notch filter 38 may be replaced with a sharp cut filter having a sharp wavelength characteristic for blocking a shorter wavelength side than the excitation light wavelength.

Figure 3:
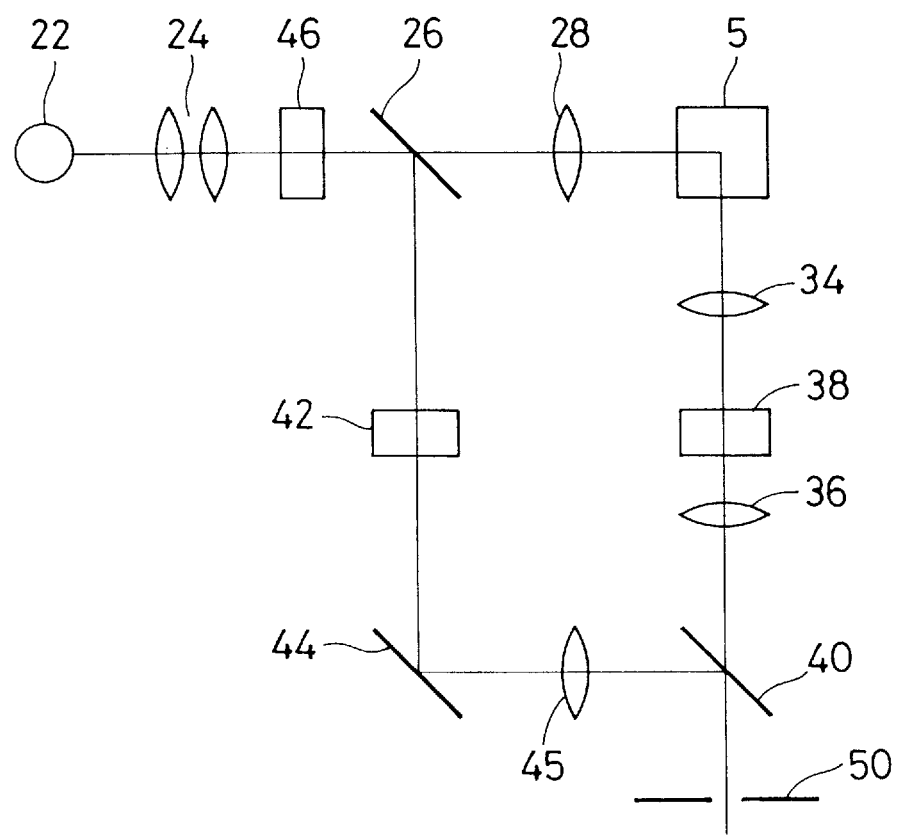
FIG. 3 is an arrangement diagram showing a measuring apparatus employing a holographic notch filter as filter means of an optical target adjusting part for receiving target light in a direction of 90 degrees to excitation light with respect to a sample.

FIG. 3 shows an embodiment employing a holographic notch filter or a cut filter as filter means of an optical target adjusting part 6 similarly to the embodiment shown in FIG. 2, while this embodiment is adapted to receive target light in a direction of 90 degrees to excitation light with respect to a sample 5. In this case, no half mirror 32 is required for irradiating the sample 5 with a sample beam 20s and introducing scattered light from the sample 5 into a condenser lens 34 of the optical target adjusting part 6. The sample beam 20s is converged by a light source condenser lens 24 and a convergent lens 28 of an excitation light source part 2 to be directly applied to the sample 5, while scattered light from the sample 5 is directly incident upon the condenser lens 34 of the optical target adjusting part 6.

While the bandpass filter 46 is arranged on the optical path of the optical correction adjusting part 8 in FIG. 2, that in FIG. 3 is arranged on an optical path of a beam from an excitation light source, which is not yet split into the sample beam 20s and a correction beam by a beam splitter 26, in the excitation light source part 2. Due to the arrangement of the bandpass filter 46 on the position shown in FIG. 3, a sideband of a laser beam can be blocked against both of the sample beam 20s and the correction beam.

While still another condenser lens 45 is arranged on an optical path of an optical correction adjusting part in FIG. 3, this lens 45, which is adapted to adjust a light quantity by condensing the correction beam on the position of a slit 50, is unnecessary if the light quantity of the correction beam is sufficiently large.

Figure 4A:
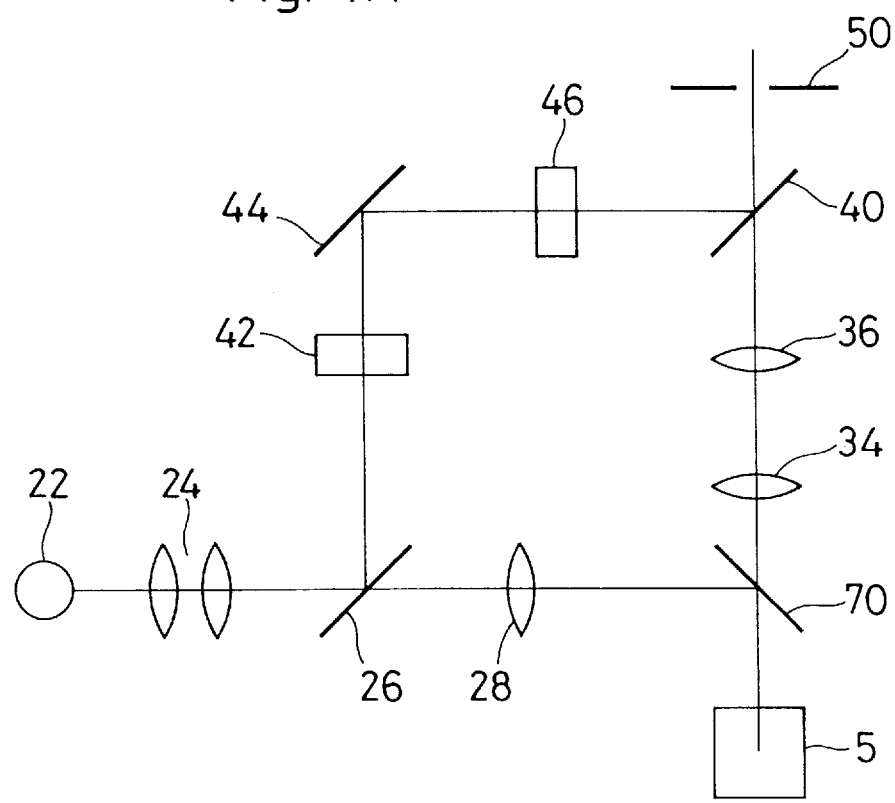
FIG. 4A is an arrangement diagram showing a measuring apparatus employing a holographic beam splitter as filter means of an optical target adjusting part for receiving target light in a direction of 180 degrees to excitation light with respect to a sample.

FIG. 4A shows an embodiment employing a holographic beam splitter 70 having characteristics of reflecting excitation light and transmitting Raman light as filter means of an optical target adjusting part 6 and receiving target light in a direction of 180 degrees to the excitation light with respect to a sample 5.

Figure 4B:
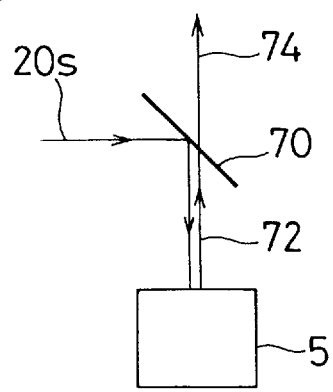
FIG. 4B is a schematic sectional view showing a holographic beam splitter part.

As shown in FIG. 4B, the holographic beam splitter 70 reflects a sample beam 20s and applies the same to the sample 5, for transmitting only target light 74 in scattered light 72, including the target light 74 and Rayleigh scattered light, from the sample 5 and introducing the same into a condenser lens 34 of the optical target adjusting part 6.

Figure 5A:
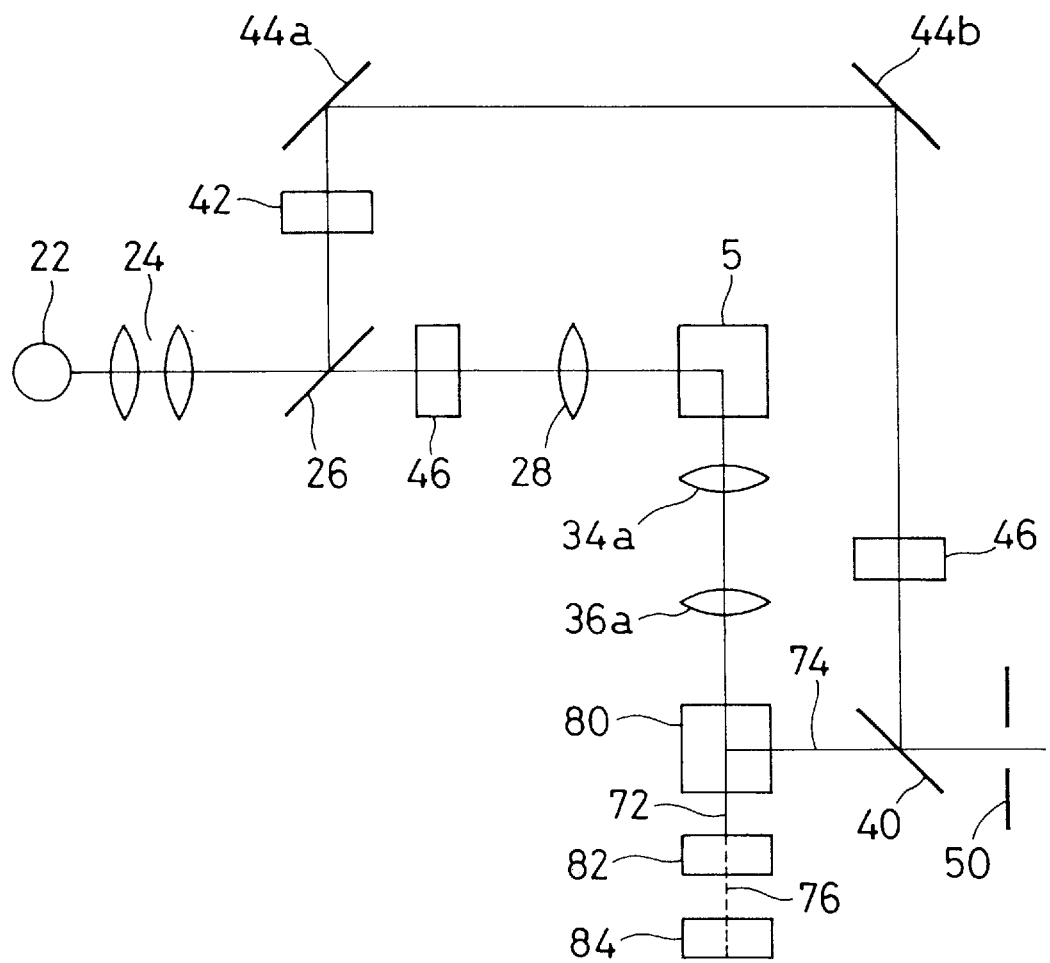
FIG. 5A is an arrangement diagram showing a measuring apparatus employing a bandpass filter as filter means of an optical target adjusting part for receiving target light in a direction of 90 degrees to excitation light with respect to a sample.

FIG. 5A shows an embodiment employing a bandpass filter 82 having characteristics of transmitting and removing an excitation light wavelength component and reflecting a target light component and receiving target light in a direction of 90 degrees to excitation light with respect to a sample 5.

Figure 5B:
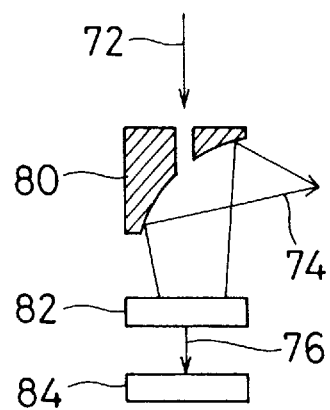
FIG. 5B is a schematic sectional view showing a bandpass filter part.

As shown in FIG. 5B, the bandpass filter 82 is arranged on a mirror face side of a transmission condensation mirror 80, while a beam stopper 84 is arranged on an opposite side of the transmission condensation mirror 80. Scattered light 72, including target light 74 and Rayleigh scattered light 76, from the sample 5 is condensed by condenser lenses 34a and 36a, to be incident upon the bandpass filter 82 from a rear surface of the transmission condensation mirror 80 through its incidence hole. In the bandpass filter 82, the Rayleigh light 76 is transmitted and absorbed by the beam stopper 84, while the target light 74 is reflected and condensed by the mirror face of the transmission condensation mirror 80, to be incident upon a spectroscope from an inlet slit 50 through a half mirror 40. A optical correction adjusting part 8 is provided with two mirrors 44a and 44b, in order to bend an optical path by 180 degrees.

Figure 6:
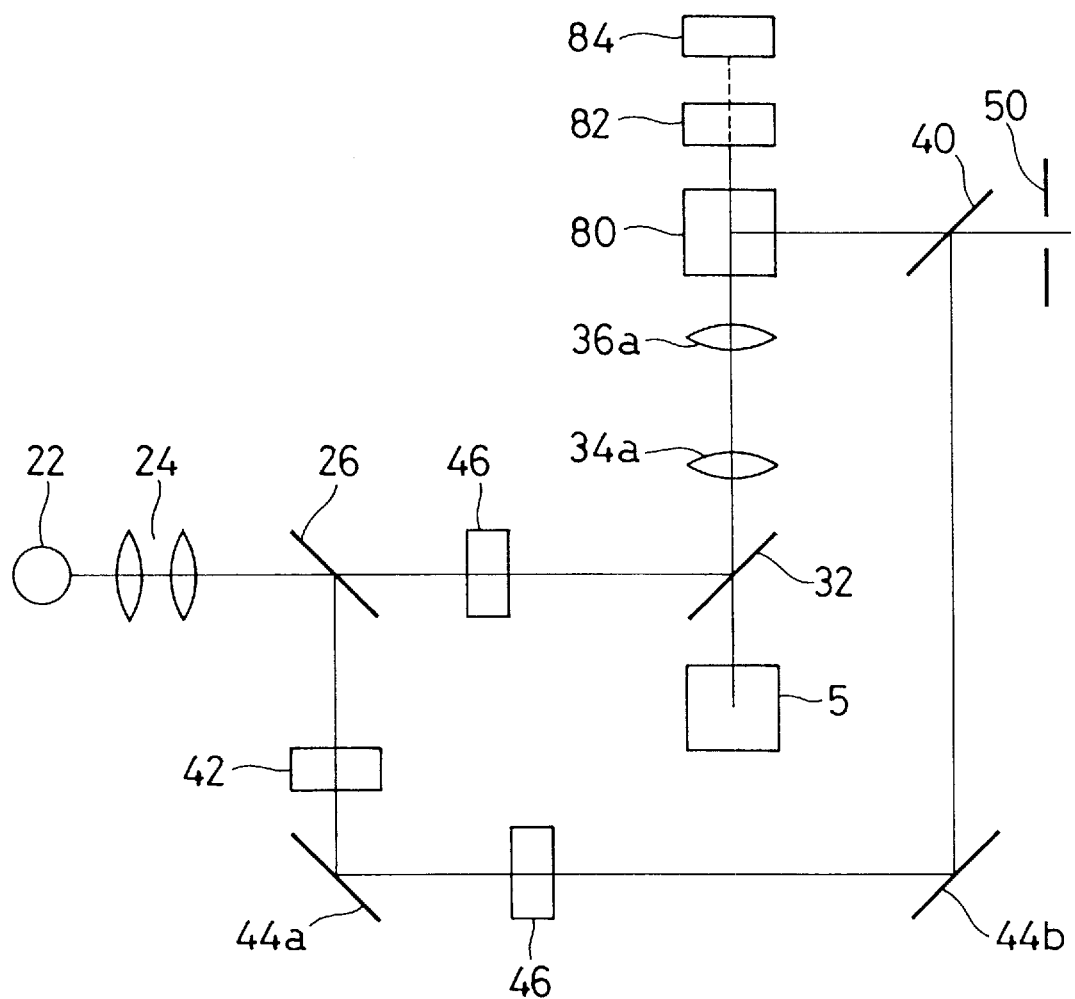
FIG. 6 is an arrangement diagram showing a measuring apparatus employing a bandpass filter as filter means of an optical target adjusting part for receiving target light in a direction of 180 degrees to excitation light with respect to a sample.

FIG. 6 shows an embodiment employing a bandpass filter 82 having characteristics of transmitting and removing an excitation light wavelength component and reflecting a target light component as filter means of an optical target adjusting part 6 similarly to that shown in FIGS. 5A and 5B, while receiving target light in a direction of 180 degrees to excitation light with respect to a sample 5. A half mirror 32 is arranged for applying a sample beam 20s to the sample 5 and introducing scattered light from the sample 5 into a condenser lens 34a of the optical target adjusting part 6.

Figure 7:
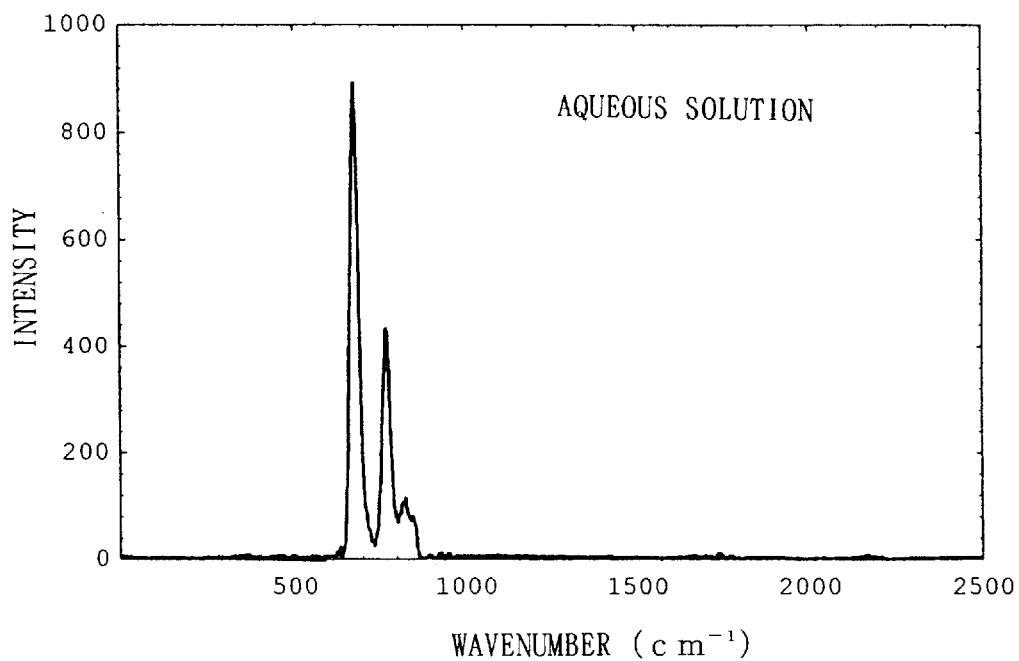
FIG. 7 illustrates a Raman spectrum of lactone mevalonate in an aqueous solution.
Figure 8:
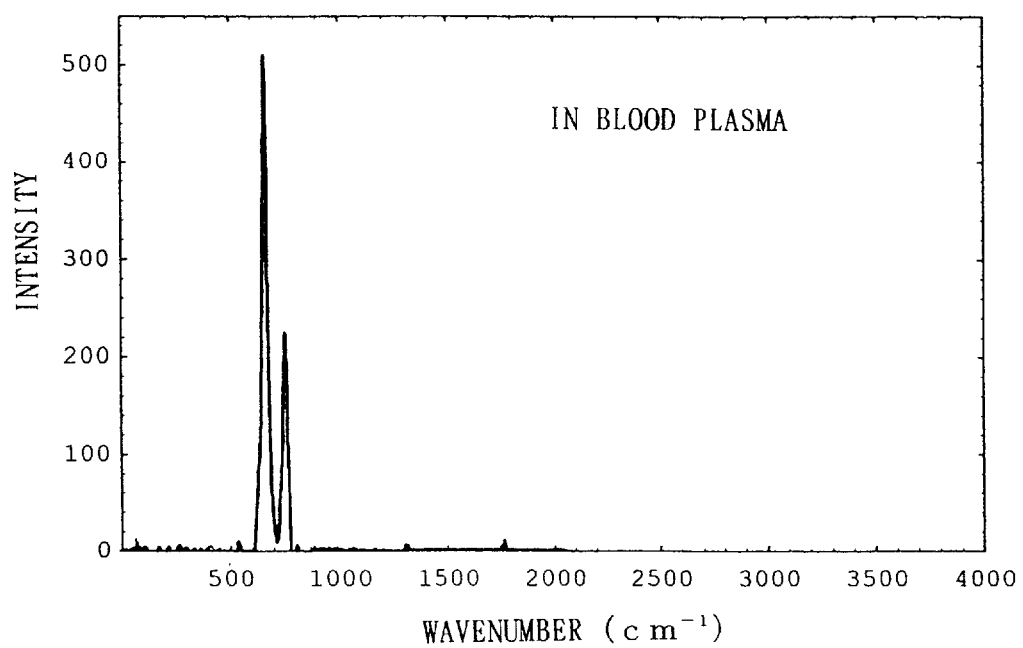
FIG. 8 illustrates a Raman spectrum of lactone mevalonate in blood plasma.
Figure 9:
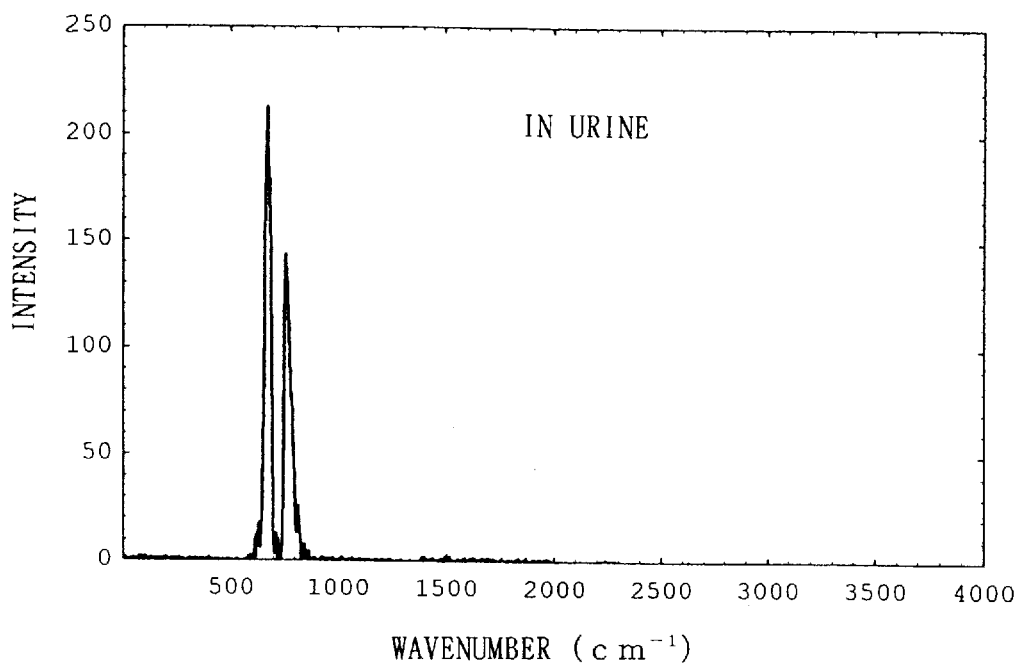
FIG. 9 illustrates a Raman spectrum of lactone mevalonate in urine.

FIGS. 7, 8 and 9 show Raman spectra of lactone mevalonate in an aqueous solution, blood plasma and urine respectively. Samples of blood plasma and urine employed for this measurement were prepared by dissolving 100 mg/ml of lactone mevalonate in blood plasma and urine respectively, while a sample of the aqueous solution was prepared by dissolving 200 mg/ml of lactone mevalonate in water. The measuring apparatus shown in FIG. 2 was employed with an excitation light source of a semiconductor laser (InGaAs laser diode SDL-531-GL by SDL, U.S.A.) for irradiating the samples with oscillation light of 802 nm as excitation light and detecting the spectra with a CCD having photosensitivity in the near infrared region. In each sample, remarkable Raman peaks appear on positions of shift wavenumbers of 680 $cm^{-1}$ and 769 $cm^{-1}$ from the excitation wavelength respectively. Peaks also exist on other wavenumber positions. Although the peaks of other wavenumber positions were detected with insufficient intensities in the measurement employing the measuring apparatus of the embodiment, there is a possibility that the same can be measured with sufficient intensities when another measuring apparatus such as an FT-Raman spectroscope is employed. Mevalonic acid can be determined also through peaks other than those at 680 cm$^{-1}$ and 769 cm$^{-1}$.

Figure 10A:
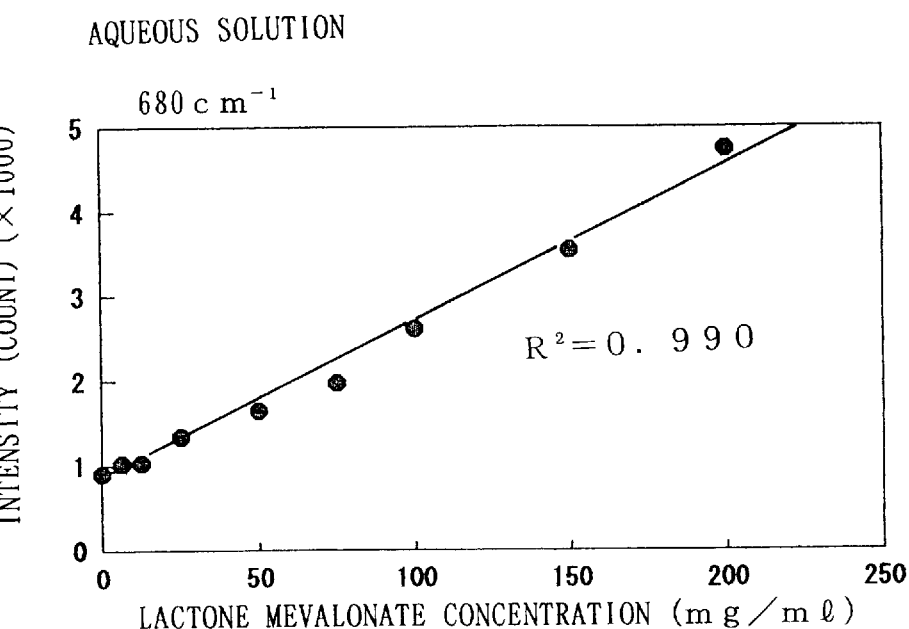
FIGS. 10A and 10B show results obtained by employing peaks at shift wavenumbers of 680 $cm^{-1}$ and 769 $cm^{-1}$ respectively, for illustrating the correlation between peak intensities and lactone mevalonate concentrations of Raman spectra in standard samples prepared by dissolving lactone mevalonate in water.
Figure 10B:
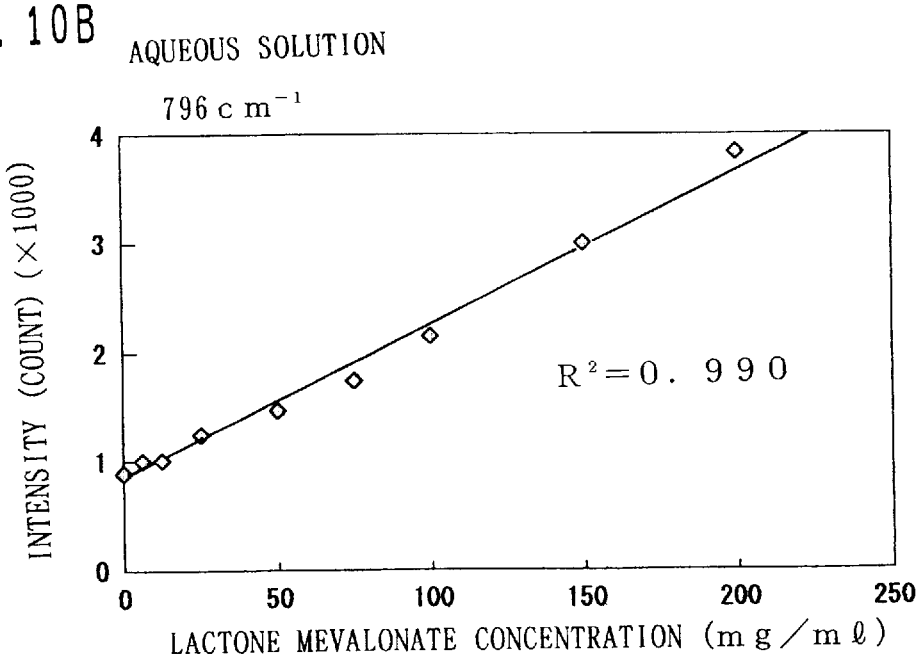

FIGS. 10A and 10B show results obtained by employing standard samples prepared by dissolving lactone mevalonate in water, varying the lactone mevalonate concentrations, and measuring correlation between peak intensities and lactone mevalonate concentrations of Raman spectra obtained as shown in FIG. 7. FIGS. 10A and 10B show results obtained by employing peaks at shift wavenumbers of 680 cm$^{-1}$ and 769 cm$^{-1}$ respectively. Correlation coefficients R$^2$ of 0.990 are obtained in FIGS. 11A and 11B respectively.

Each correlation coefficient R$^2$ is obtained by squaring a correlation coefficient R expressed as follows:

$$R = \frac{\sum_{i=1}^{n}(xi-X)(yi-Y)}{\sqrt{\sum_{i=1}^{n}(xi-X)^2 \cdot \sum_{i=1}^{n}(yi-Y)^2}}$$

where xi represents the concentration of each measuring point of each sample, yi represents the target light intensity with respect to xi, X represents an average value of concentrations of the respective measuring points of each sample, and Y represents an average value of the target light intensities.

Figure 11A:
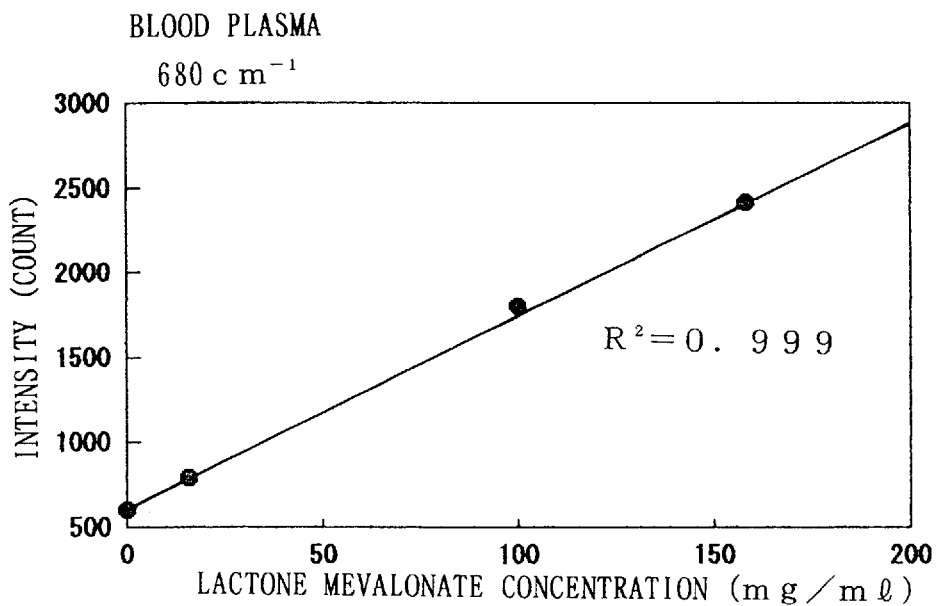
FIGS. 11A and 11B show results employing peaks at shift wavenumbers of 680 $cm^{-1}$ and 769 $cm^{-1}$ respectively, for illustrating the correlation between peak intensities and lactone mevalonate concentrations of Raman spectra in standard samples prepared by dissolving lactone mevalonate in blood plasma.
Figure 11B:
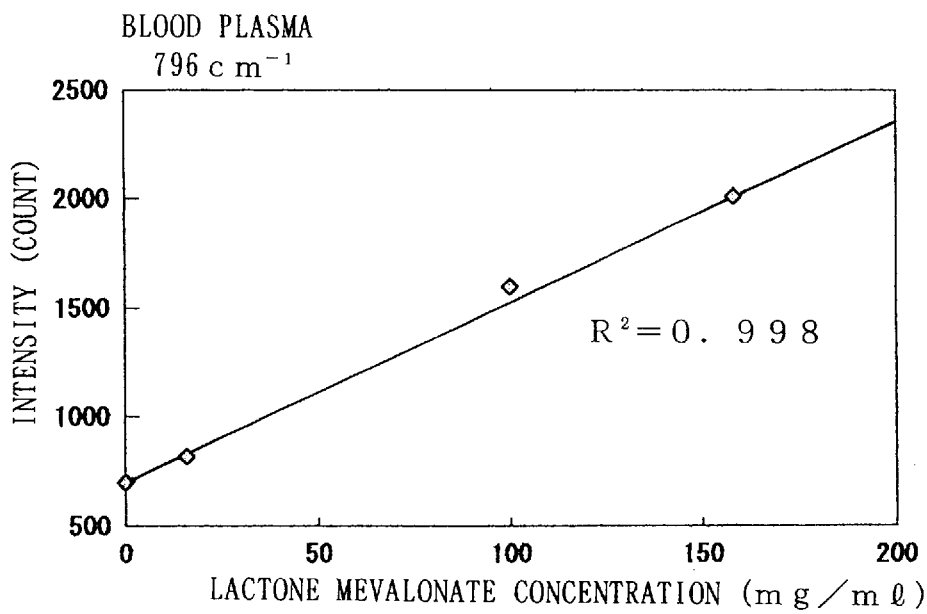

FIGS. 11A and 11B show results obtained by employing standard samples prepared by dissolving lactone mevalonate in blood plasma, varying the lactone mevalonate concentrations, and measuring correlation between peak intensities and lactone mevalonate concentrations of Raman spectra obtained as shown in FIG. 8. FIGS. 11A and 11B show results obtained by employing peaks at shift wavenumbers of 680 cm$^{-1}$ and 769 cm$^{-1}$ respectively. Correlation coefficients R$^2$ of 0.999 and 0.998 are obtained in FIGS. 11A and 11B respectively.

FIGS. 12A and 12B show results obtained by employing standard samples prepared by dissolving lactone mevalonate in urine, varying the lactone mevalonate concentrations, and measuring correlation between peak intensities and lactone mevalonate concentrations of Raman spectra obtained as shown in FIG. 9. FIGS. 12A and 12B show results obtained by employing peaks at shift wavenumbers of 680 cm$^{-1}$ and 769 cm$^{-1}$ respectively. Correlation coefficients R$^2$ of 0.998 and 0.963 are obtained in FIGS. 12A and 12B respectively.

A mevalonic acid concentration in an aqueous solution, blood plasma or urine can be determined by utilizing such correlation as a calibration curve.

In actual measurement, a sample is prepared from blood plasma or urine so that acid such as hydrochloric acid, sulfuric acid or perchloric acid is added thereto or acid treatment is performed with solid acid (ion exchange resin etc.) for converting mevalonic acid contained in the sample to lactone mevalonate and thereafter measuring Raman scattered light.

Although the present invention has been described and illustrated in detail, it is clearly understood that the same is by way of illustration and example only and is not to be taken by way of limitation, the spirit and scope of the present invention being limited only by the terms of the appended claims.

We claim:

1. An optical measuring method of determining mevalonic acid comprising the steps of:
   converting mevalonic acid being contained in a sample to lactone mevalonate, and
   measuring generated Raman scattered light from said sample while irradiating said sample with Raman excitation light.

2. The optical measuring method in accordance with claim 1, wherein
   acid treatment is performed on said sample for converting said mevalonic acid to lactone mevalonate.

3. The optical measuring method in accordance with claim 2, wherein
   acid being employed for said acid treatment is hydrochloric acid.

4. The optical measuring method in accordance with claim 2, wherein
   acid being employed for said acid treatment is hydrogen chloride gas.

5. The optical measuring method in accordance with claim 1, wherein
   said Raman excitation light is near infrared light.

6. The optical measuring method in accordance with claim 1, wherein
   said Raman excitation light is near infrared light, and
   acid treatment is performed on said sample for converting said mevalonic acid to lactone mevalonate.

7. The optical measuring method in accordance with claim 1, wherein
   a wavenumber for said excitation light having correlation between a lactone mevalonate concentration and a Raman spectral intensity is selected, and
   said sample is irradiated with said Raman excitation light, and the mevalonic acid concentration of said sample is determined through a calibration curve being previously formed between said Raman spectral intensity and said lactone mevalonate concentration at said wavenumber.

8. The optical measuring method in accordance with claim 7, wherein
   said Raman excitation light is near infrared light.

9. The optical measuring method in accordance with claim 7, wherein
   said Raman excitation light is near infrared light, and
   acid treatment is performed on said sample for converting said mevalonic acid to lactone mevalonate.

10. The optical measuring method in accordance with claim 1, wherein
    a wavenumber for said excitation light having correlation between a lactone mevalonate concentration and a Raman spectral intensity is selected,
    said sample is irradiated with said Raman excitation light, and the mevalonic acid concentration of said sample is determined through a calibration curve being previously formed between said Raman spectral intensity and said lactone mevalonate concentration at said wavenumber, and
    said wavenumber is selected selected from the group consisting of 650 to 700 cm$^{-1}$, 730 to 790 cm$^{-1}$, 1000 to 1100 cm$^{-1}$, 1100 to 1190 cm$^{-1}$, 1220 to 1300 cm$^{-1}$, 1320 to 1500 cm$^{-1}$, 1690 to 1750 cm$^{-1}$ and 2900 to 3000 cm$^{-1}$.

11. The optical measuring method in accordance with claim 10, wherein
    said Raman excitation light is near infrared light.

12. The optical measuring method in accordance with claim 10, wherein
    said Raman excitation light is near infrared light, and
    acid treatment is performed on said sample for converting said mevalonic acid to lactone mevalonate.

* * * * *